United States Patent [19]

Thiberg

[11] Patent Number: 5,800,479
[45] Date of Patent: *Sep. 1, 1998

[54] DEVICE FOR MEDICAL EXTERNAL TREATMENT BY MEANS OF LIGHT

[75] Inventor: Rolf Thiberg, Åkersberga, Sweden

[73] Assignee: Biolight Patent Holding AB, Danderyd, Sweden

[*] Notice: The term of this patent shall not extend beyond the expiration date of Pat. No. 5,766,233.

[21] Appl. No.: 676,216

[22] PCT Filed: Jan. 19, 1995

[86] PCT No.: PCT/SE95/00049

§ 371 Date: Jul. 18, 1996

§ 102(e) Date: Jul. 18, 1996

[87] PCT Pub. No.: WO95/19810

PCT Pub. Date: Jul. 27, 1995

[30] Foreign Application Priority Data

Jan. 20, 1994 [SE] Sweden .................... 9400153
Aug. 10, 1994 [SE] Sweden .................... 9402679

[51] Int. Cl.$^6$ .................................................. A61N 5/06
[52] U.S. Cl. .................................. 607/88; 606/2; 606/9
[58] Field of Search ........................ 607/88–91, 93; 315/174, 246, 324; 606/1, 3, 9

[56] References Cited

U.S. PATENT DOCUMENTS

| | | | |
|---|---|---|---|
| 4,930,504 | 6/1990 | Diamantopoulos et al. | 128/395 |
| 5,259,380 | 11/1993 | Mendes et al. | 607/115 |
| 5,304,207 | 4/1994 | Stromer | 607/88 |
| 5,456,700 | 10/1995 | Horiguchi | 607/88 |
| 5,549,660 | 8/1996 | Mendes et al. | 607/88 |

FOREIGN PATENT DOCUMENTS

WO9309847  5/1993  WIPO.

OTHER PUBLICATIONS

Uppfinnaren & Kunstruktionen, vol. No. 2, 1993, P.A. Bengtsson, "Uppfinningen som botar sjukdomar med vanligt ljus."

Primary Examiner—Jennifer Bahr
Assistant Examiner—Bryan K. Yarnell
Attorney, Agent, or Firm—Alfred J. Mangels

[57] ABSTRACT

A device for the external medical treatment with the aid of light, including a light emitting element which is intended to lie against or be held close to a wound or sore on the body of an individual, and a drive arrangement for driving the light emitting element, wherein the light emitting element includes light emitting diodes or like devices and is constructed to emit infrared light. The arrangement (8, 9, 19) is constructed to cause the light emitting element (1) to emit infrared light in a first stage for a first predetermined length of time and thereafter to emit visible light in a second stage for a second predetermined length of time. The drive arrangement (8, 9, 10) is also constructed to cause the light emitting element (1) to pulsate the emitted infrared light and the emitted visible light respectively in accordance with a predetermined series of pulse frequencies over the predetermined time periods. The drive arrangement is constructed to emit two or more series having successively rising frequencies F1, F2, Fn, where F1 is a fundamental frequency and where F2, Fn are multiples of the fundamental frequency.

13 Claims, 1 Drawing Sheet

DEVICE FOR MEDICAL EXTERNAL TREATMENT BY MEANS OF LIGHT

BACKGROUND OF THE INVENTION

1. Field of the Invention

The present invention relates to a device for the external medicinal treatment with the aid of light, more specifically with light which will alleviate and/or cure different sickness conditions.

2. Description of the Related Art

It has been observed that infrared light has a beneficial effect.

Swedish Patent Specification . . . (patent application no 9400153-4) describes a device for healing wounds and sores with the aid of light. The device includes a light emitting element which is intended to lie against or to be held close to a wound, or sore, on the body of an individual, and means for powering the light emitting element, wherein the light emitting element includes light emitting diodes or like devices and is constructed to emit infrared light. The invention according to this patent is characterized in that the power means is adapted to cause the light emitting element to emit infrared light in a first stage for a first predetermined length of time, and then to emit visible red light in a second stage for a second predetermined length of time, and in that the power means is constructed to cause the light emitting element to pulsate the emitted infrared light and the visible red light respectively in accordance with a predetermined series of pulse frequencies during said time periods.

It has thus been observed that infrared light shall be combined with the emission of a visible red light, by emitting the different lights sequentially, one after the other. It has also been observed that the different lights shall be emitted in pulse form having certain pulse repetition frequencies.

It has now been found that a device of this kind can be used very successfully for treating other sicknesses, illnesses and injuries, such as injuries resulting from sporting activities, stretched muscles, myalgia, joint pains or arthralgia, headaches, different inflammatory conditions, different skin complaints, such as acne, back pains, etc., provided that the lights are emitted, or transmitted, in a given manner. In this regard, the light treatment has a favorable effect on the healing process of injuries, and will also ease and/or cure different sicknesses and illnesses.

SUMMARY OF THE INVENTION

The present invention is based on the understanding that light treatment effected by emitting a given light in a given frequency series will provide a significantly improved effect, by shortening the time taken to cure or ease an illness or sickness.

The present invention thus relates to a device for the external medical treatment with the aid of light. The device includes a light emitting element which is intended to lie against or be held close to a wound or sore on the body of an individual, and a power source for powering the light emitting element. The light emitting element includes light emitting diodes or the like and emits infrared light. The power source is constructed to cause the light emitting element to emit infrared light in a first stage for a first predetermined length of time, and thereafter to cause the light emitting element to emit visible light in a second stage for a second predetermined length of time. The power source is also constructed to cause the light emitting element to pulsate the emitted infrared light and the visible light respectively in accordance with a predetermined series of pulse frequencies over said predetermined time periods, and to emit two or more series of successively rising frequencies F1, F2, Fn, where F1 is a fundamental frequency and where F2, Fn are multiples of the fundamental frequency.

BRIEF DESCRIPTION OF THE DRAWINGS

The invention will now be described in more detail, partly with reference to an exemplifying embodiment of the invention illustrated in the accompanying drawing, in which.

DESCRIPTION OF THE PREFERRED EMBODIMENTS

Figure 1:
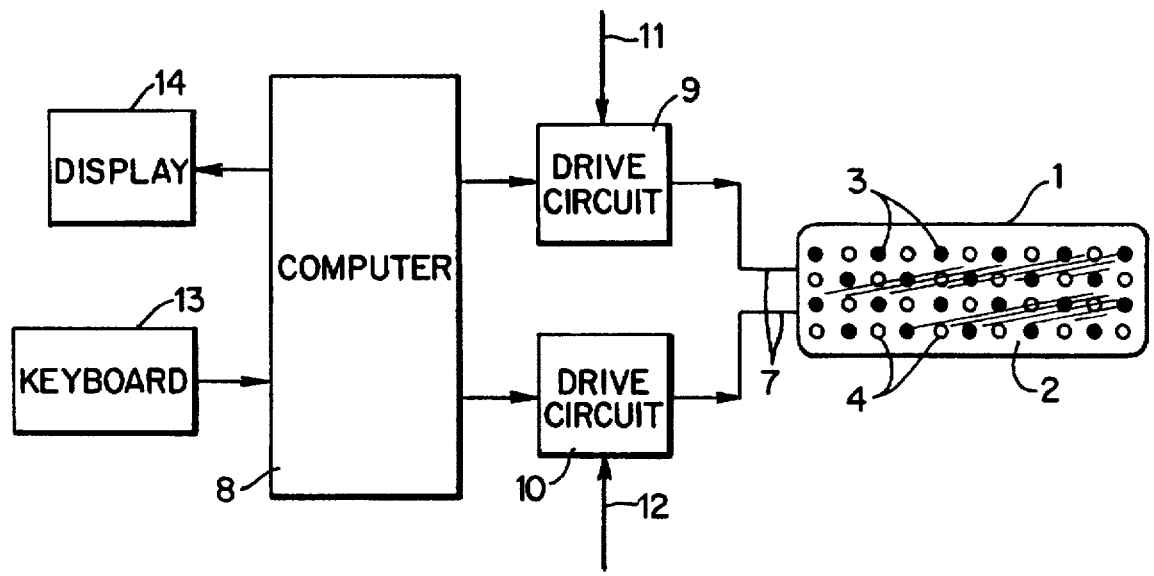
FIG. 1 is a block schematic illustrating the device.
Figure 2:
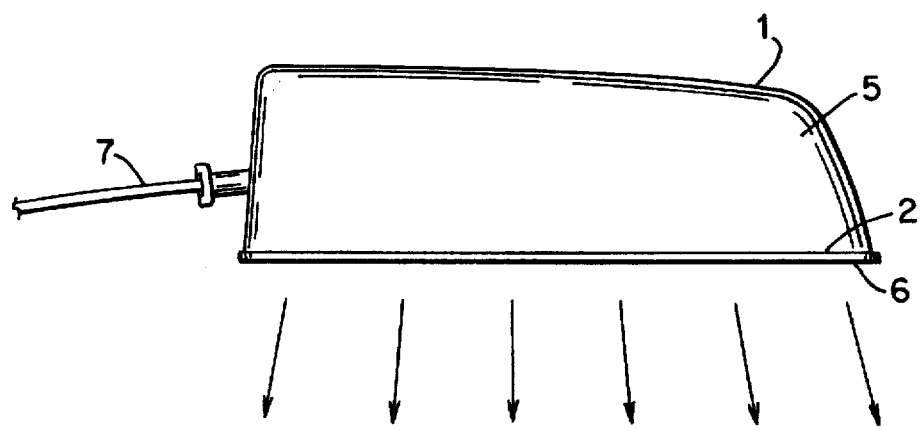
FIG. 2 is a side view of a light emitting element.

FIGS. 1 and 2 illustrate a device for healing wounds and sores with the aid of light, said device including a light emitting element 1 which is intended to be placed against or held close to the body of an individual. The light emitting element is shown from one side in FIG. 2 and from beneath in FIG. 1. This element includes a housing 5 which is provided with a transparent plate 6. Above the plate 6 there is located a surface 2 in which a number of light emitting diodes 3, 4 or corresponding devices are mounted. Thus, the light emitting diodes are intended to transmit light through the plate 6 when activated, i.e. when supplied with current through a cable 7. In use, the housing 5 is held so that the plate 6 will lie against the part of the body to be treated. The device also includes drive means 8, 9, 10 for driving the light emitting element 1. The light emitting element 1 includes light emitting diodes 3 or like devices which are constructed to emit infrared light. These diodes are marked with solid circles in FIG. 1.

The drive means 8, 9, 10 are constructed to cause the light emitting element 1 to emit infrared light in a first stage for a first predetermined length of time, and then to emit visible light in a second stage for a second predetermined length of time. Visible light is emitted by means of light emitting diodes 4 or like devices. These devices are marked with hollow circles in FIG. 1. It is extremely important that the treatment is carried out in the order infrared light followed by visible light.

According to the present invention, the drive means 8, 9, 10 are also constructed to cause the light emitting element 1 to pulsate the emitted infrared light and the visible light respectively in accordance with a predetermined series of pulse frequencies over the aforesaid predetermined time periods.

According to the present invention, the drive means are also constructed to transmit two or more series of successively rising frequencies F1, F2, Fn, where F1 is a fundamental frequency and where F2, Fn are multiples of the fundamental frequency.

According to a much preferred embodiment, the fundamental frequency is 7.8 Hz.

According to another highly preferred embodiment, the fundamental frequency is 8.6 Hz.

The drive means include a computer 8 and associated memory, and drive circuits 9, 10 which are controlled by the computer. These drive circuits 9, 10 are supplied with voltage for powering the light emitting diodes 3, 4, through conductors 11, 12. One drive circuit, 9, is intended to activate the infrared light emitting diodes 3 and the other drive circuit 10, is intended to activate the light emitting diodes 4 that emit visible light. The computer and the drive circuits are of a suitable known kind.

The infrared light emitting diodes 3 are preferably GaAs-type semi-conductors (gallium arsenide) which emit light having a wavelength of 950 nanometers. The light emitting diodes 4 which emit visible light are preferably of the GaAs-type which emit visible light.

According to one preferred embodiment of the invention, the light emitting diodes are present in the light emitting element in such numbers that the infrared light emitting diodes together deliver a light power of 1800 milliwatts, while the visible light emitting diodes together deliver a light power of 3000 millicandela.

Mention is made in the aforegoing of predetermined lengths of times over which light is emitted during a treatment. According to one preferred embodiment, these predetermined time periods are approximately of equal duration. Furthermore, the predetermined time period lies in a range of 2–4 minutes, preferably 3 minutes.

Mention is made in the aforegoing of a series of pulse frequencies. According to one preferred embodiment, each series is comprised of three mutually sequential pulse frequencies F1, F2 and F3 at which respective light is emitted.

In summary, this means that there is first emitted solely infrared light, said light being emitted so as to be pulsed in a manner such that there is first emitted light which is pulsed at a given pulse frequency, whereafter the light is emitted while pulsed at a second pulse frequency, and then at a third pulse frequency. Thereafter there is emitted only visible light, this light being pulsed at a first pulse frequency and then at a second pulse frequency and thereafter at a third pulse frequency.

Provided that the predetermined time period is three minutes, infrared light is emitted over a period of three minutes, and is then followed by visible light over a period of three minutes. Preferably, the duration of each pulse frequency in the series is one minute.

According to one highly preferred embodiment, the light emitting element 1 includes red light emitting diodes 4 which emit visible light at the wavelength of 660 nanometers.

According to another preferred embodiment, the light emitting element 1 includes light emitting diodes 4 which are constructed to emit an essentially monochromatic visible light in one of the colors blue, yellow, orange or green.

The visible light that is used will depend on the sickness, illness or the nature of the injury to be treated.

According to another preferred embodiment of the invention, the first series of pulse frequencies is 78+/−10 Hz, 702+/−20 Hz and 8.58 KHz+/−100 Hz. This means that there is first pulsed the infrared light at a pulse frequency of 78 Hz, followed by a pulse frequency of 702 Hz and then a pulse frequency of 8.58 KHz, whereafter visible red light is emitted in accordance with the same series.

A typical treatment process is effected by turning the light emitting element to face the injured part of the body or that part which is relevant to the illness in question, and infrared light is emitted in accordance with the aforesaid series for a total period of three minutes, whereafter visible light is also emitted in accordance with said series for a total period of three minutes. Treatment thus takes six minutes. The treatment is repeated from two to three times each week. Typically, the effect of the treatment will be seen after 4–6 treatments.

According to one preferred embodiment, the infrared light and the visible red light respectively are emitted in accordance with another pulse frequency series after from 4 to 6 treatments using the aforementioned series. According to this embodiment, the drive means 8, 9, 10 is intended to cause the light emitting element 1 to emit a second series of pulse frequencies, this second pulse frequency series being, for instance, 15.6+/−3 Hz, 289+/−20 Hz and 31.2+/−5 Hz. Each type of light is preferably emitted for a total period of three minutes also with this second pulse frequency series.

In the aforegoing, pulse frequency series have been mentioned in which the pulse frequency is given a relatively narrow interval. It is important that the pulse frequency is the nominal frequency or very close thereto. However, the aforesaid predetermined time periods can be varied slightly.

Connected to the computer 8 is a keyboard 13 by means of which relevant series and the duration of said series can be chosen by depressing the appropriate keys. There will preferably be found a number of different preprogrammed treatment programs to choose from. To the computer 8 there is also connected to a display 14 which presents desired data, such as the treatment program chosen, the time duration of the series, etc.

It will be understood that the construction of the light emitting element can be changed, and that the number and the power of the light emitting diodes can also be changed. The control circuit that includes the computer can also be modified.

The present invention cannot therefore be considered restricted to the aforedescribed exemplifying embodiments, since the variations and modifications can be made within the scope of the following claims.

What is claimed is:

1. A device for the external medical treatment of a patient with the aid of light, said device comprising:

a) a light emitting element for positioning adjacent a wound or sore on the body of a person, the light emitting element including a source of infrared light and a source of visible light; and b) drive means for driving the light emitting element, the drive means including a timer for causing the light emitting element to emit only infrared light during a first treatment stage for a first predetermined period of time and thereafter to emit only visible light during a second stage for a second predetermined period of time, and including pulsation means for pulsating the emitted infrared light and the emitted visible light at a predetermined series of pulsation frequencies over the respective predetermined time periods, wherein the pulsation frequencies are defined by successively increasing frequencies F1, F2, Fn, wherein F1 is a fundamental frequency and wherein F2, Fn are multiples of the fundamental frequency.

2. A device according to claim 1, wherein the fundamental frequency is about 7.8 Hz.

3. A device according to claim 1, wherein the fundamental frequency is about 8.6 Hz.

4. A device according to claim 1, wherein the first and second predetermined time periods are substantially of equal duration; and wherein each time period is between about 2–4 minutes.

5. A device according to claim 4, wherein the predetermined time periods are substantially 3 minutes.

6. A device according to claim 1, wherein each of said series of pulse frequencies includes three sequential pulse frequencies at which light is emitted.

7. A device according to claim 1, wherein a first series of pulse frequencies is 78+/−10 Hz, 702+/−20 Hz and 8.58 KHz+/−100 Hz.

8. A device according to claim 7, wherein a second series of predetermined pulse frequencies is 15.6+/−3 Hz, 289+/−20 Hz and 31.2+/−5 Hz.

9. A device according to claim 1, wherein the light emitting element includes infrared light emitting diodes which emit light having a wavelength of about 950 nanometers.

10. A device according to claim 9, wherein the infrared light emitting diodes produce a total light power of about 1800 milliwatts.

11. A device according to claim 1, wherein the light emitting element includes red light emitting diodes which emit light having a wavelength of about 660 nanometers.

12. A device according to claim 11, including infrared light emitting diodes which emit light having a wavelength of about 950 nanometers, wherein the infrared light emitting diodes produce a total light power of about 1800 milliwatts and the red light emitting diodes produce a total light power of about 3000 millicandela.

13. A device according to claim 1, wherein the source of visible light includes a plurality of light emitting diodes which emit an essentially monochromatic visible light having a color selected from the group consisting of the colors blue, yellow, orange, and green.

* * * * *